United States Patent [19]

Arav

[11] Patent Number: 5,715,686
[45] Date of Patent: Feb. 10, 1998

[54] METHOD FOR CRYOPRESERVATION OF BIOLOGICAL SAMPLES

[75] Inventor: Amir Arav, Tel Aviv, Israel

[73] Assignee: State of Israel, Bet Dagan, Israel

[21] Appl. No.: 743,435

[22] Filed: Nov. 1, 1996

[51] Int. Cl.$^6$ .................................................... F17C 5/00
[52] U.S. Cl. ........................ 62/54.1; 62/78; 62/100
[58] Field of Search ................ 62/54.1, 100, 268, 62/78

[56] References Cited

U.S. PATENT DOCUMENTS

| | | | |
|---|---|---|---|
| 3,994,141 | 11/1976 | Schrawer | 62/54.1 |
| 4,302,950 | 12/1981 | Sitte | 62/78 |
| 4,827,737 | 5/1989 | Oda et al. | 62/78 |
| 4,840,034 | 6/1989 | Liberman | 62/78 |

OTHER PUBLICATIONS

Mazur et al: "Cryobiological Preservation of Drosophila Embryos"; Science, vol. 258, pp. 1932–1935 (1992).

*Primary Examiner*—Ronald C. Capossela
*Attorney, Agent, or Firm*—Mark M. Friedman

[57] ABSTRACT

A method for cryopreservation of biological samples. A cryogenic liquid such as liquid nitrogen is turned into a slush within a container such as a standard cryogenic storage vial by applying suction to create a partial vacuum above the liquid. The sample to be cooled is dropped into the slush and is subsequently stored in the container within which it was cooled.

7 Claims, 1 Drawing Sheet

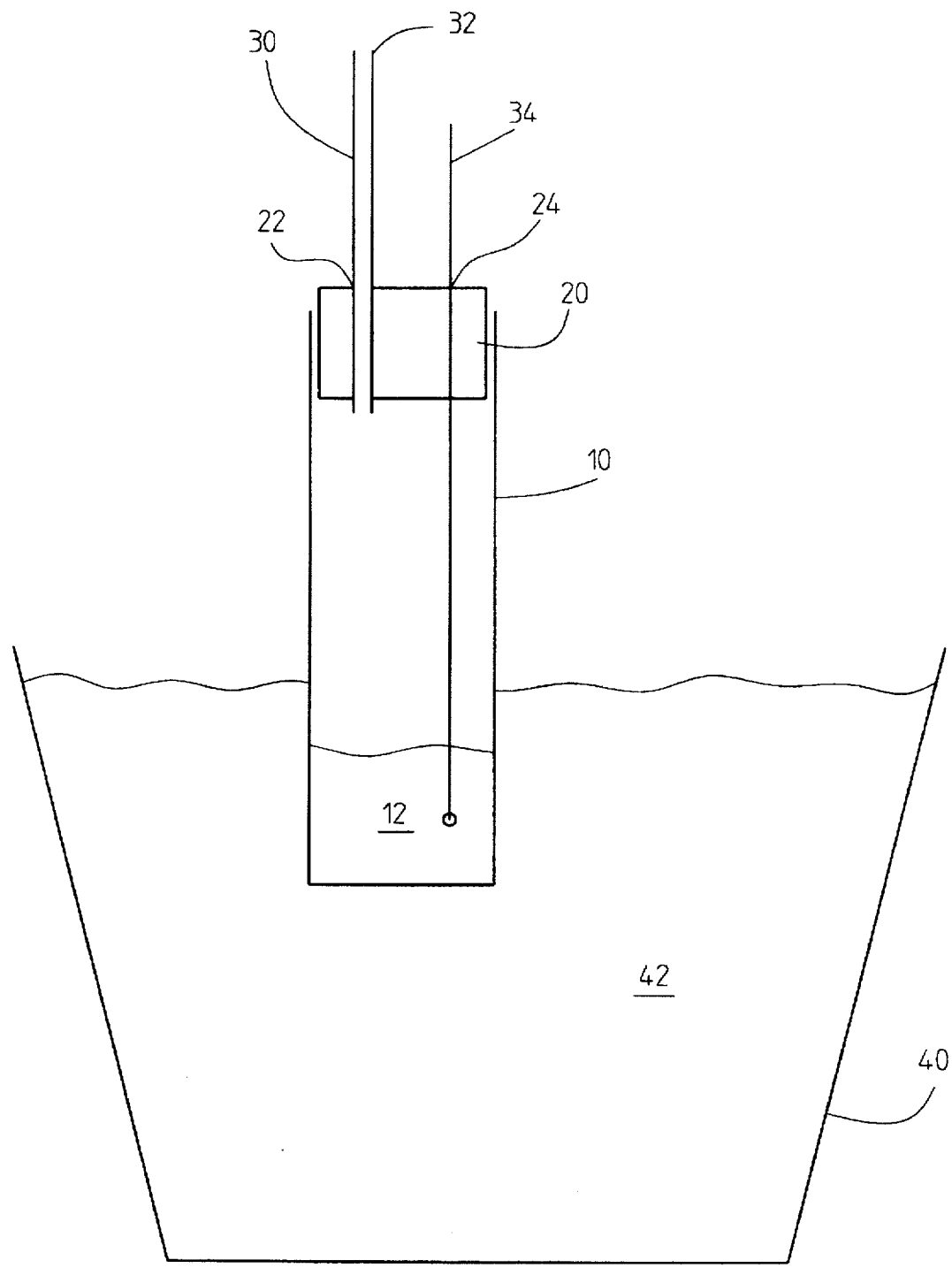
FIGURE

METHOD FOR CRYOPRESERVATION OF BIOLOGICAL SAMPLES

FIELD AND BACKGROUND OF THE INVENTION

The present invention relates to a method for cryopreservation of a biological sample in a cryogenic fluid and, more particularly, to a method for vitrification of the samples in which heat is transferred from the sample to the cryogenic fluid more efficiently than has been possible heretofore.

Biological samples commonly are vitrified by immersing them in liquid nitrogen. Typically, the liquid nitrogen used is in equilibrium with its vapor, at its boiling temperature of about −196° C. When the sample is placed in the liquid nitrogen, heat flows from the sample to the liquid nitrogen, causing the liquid nitrogen to boil in the immediate vicinity of the sample, thereby creating a pocket of nitrogen vapor around the sample. Conduction of heat through the nitrogen vapor is much less efficient than conduction of heat through the liquid nitrogen. Therefore, the vapor pocket that surrounds the sample insulates the sample from the liquid nitrogen and retards further heat transfer. Therefore, biological samples to be vitrified must be surrounded by a highly concentrated solution of a cryoprotectant. These cryoprotectants are compounds, such as polyhydrated alcohols, that tend to be toxic in concentrations effective for cryopreservation. Biological samples surrounded by a cryoprotectant solution that is sufficiently dilute to be non-toxic commonly suffer thermal damage because of the internal thermal gradient that exists between the cold sample periphery and the warmer sample interior while heat is conducted slowly through the vapor pocket.

One method that has been used to inhibit the formation of the vapor pocket is to lower the temperature of the liquid nitrogen below its boiling point, by applying suction to create a partial vacuum in the vapor above the liquid nitrogen. This causes some of the nitrogen to solidify, creating a nitrogen slush at the melting temperature of nitrogen, about −210° C. A sample immersed in nitrogen slush remains surrounded by liquid as it solidifies. Using this method, Peter Mazur and colleagues (Mazur, P., Cole, K. W., Hall, W. H., Schreuders, P. D., Mahowald, A. P., Cryobiological preservation of Drosophila embryos, Science, vol. 258 pp. 1932–1935 (1992)) were able to vitrify and subsequently revive whole drosophila embryos. The conduction of heat from the sample to the nitrogen slush is sufficiently rapid to enable the vitrification of biological samples using dilute cryoprotectant solutions.

Nevertheless, this method is not as efficient as it could be, notably because the sample must be held by a holder, for example a forceps, while it is immersed in the slush, and then removed from the slush and transferred to a liquid-nitrogen-filled cryogenic vial for storage. Both the sample and the forceps are cooled by the slush. Thus the rate of heat transfer from the sample to the slush is not as great as it would be if only the sample were in contact with the slush. This imposes an unnecessarily restrictive upper limit on the cooling rate and cryoprotectant concentration that may be used in connection with this method.

There is thus a widely recognized need for, and it would be highly advantageous to have, a method for freezing a biological sample in nitrogen slush in which only the sample contacts the slush.

SUMMARY OF THE INVENTION

According to the present invention, there is provided a method for the cryopreservation of a sample, comprising the steps of: (a) providing a container partially filled with a first cryogenic liquid; (b) imposing a partial vacuum above the first liquid, thereby creating a slush; and (c) dropping the sample into the slush.

The principle of the present invention is to create the cryogenic slush in the container in which the frozen sample is to be stored, and to drop the sample into the slush. In this way, the entire outer surface of the sample contacts the cryogenic liquid, optimizing heat transfer from the sample to the slush.

An additional advantage of the present invention is that the vitrified sample may be subsequently stored in the same container as the one in which it was vitrified.

BRIEF DESCRIPTION OF THE DRAWING

The invention is herein described, by way of example only, with reference to the accompanying drawing, wherein the sole FIGURE is a schematic cross-sectional diagram of a preferred device for implementing the method of the present invention.

DESCRIPTION OF THE PREFERRED EMBODIMENTS

The present invention is of a method for vitrification or rapid freezing biological samples. Specifically, the present method can be used to vitrify biological samples in less concentrated cryoprotectant solution than can be used by the prior art methods.

The principles and operation of a cryopreservation method according to the present invention may be better understood with reference to the drawing and the accompanying description.

Referring now to the drawing, the sole FIGURE is a schematic cross-sectional diagram of a preferred device for implementing the method of the present invention. A standard cryogenic storage vial 10 is partially filled with liquid nitrogen 12, and is partially immersed in a larger bath 40 of liquid nitrogen 42 for extra thermal stability. Vial 10 is provided with a rubber stopper 20. Vial 10 is sealed by inserting stopper 20 into the open end of vial 10, and is opened by removing stopper 20 from the open end of vial 10. A hollow needle 30, inserted through stopper 20 via a hole 22, and having a proximal end 32 that is outside of vial 10 when vial 10 is sealed by stopper 20, provides access to the vapor above liquid nitrogen 12. A thermocouple 34, inserted through a hole 24 in stopper 20, is provided for monitoring the temperature of liquid nitrogen 12.

In use, suction is applied to proximal end 32 of needle 30 to convert liquid nitrogen 12 into a slush. Preferably, the partial vacuum thus created above liquid nitrogen 12 has a pressure of about 600 millimeters of mercury. Stopper 20 is removed from vial 10, the biological sample, sitting on an electron microscope grid, is dropped into the slush, and stopper 20 is reinserted into the open end of vial 10. Optionally, further suction may be applied to proximal end 32 of needle 30 to keep the slush at the melting temperature of nitrogen.

While the invention has been described with respect to a limited number of embodiments, it will be appreciated that many variations, modifications and other applications of the invention may be made.

What is claimed is:

1. A method for the cryopreservation of a sample, comprising the steps of:
   (a) providing a container partially filled with a first cryogenic liquid;

(b) imposing a partial vacuum above said first liquid, thereby creating a slush;

(c) opening said container; and (d) dropping the sample into said slush.

2. The method of claim 1, wherein said first cryogenic liquid includes liquid nitrogen.

3. The method of claim 1, wherein said partial vacuum has a pressure of about 600 millimeters of mercury.

4. The method of claim 1, further comprising the step of imposing a partial vacuum above said slush.

5. The method of claim 1, wherein said partial vacuum is imposed by the steps of:

(i) providing said container with a cap having a hollow needle inserted therethrough, said needle having a proximal end outside of said container; and (ii) applying suction to said proximal end.

6. The method of claim 1, further comprising the step of partially immersing said container in a second cryogenic liquid.

7. The method of claim 6, wherein said second cryogenic liquid includes liquid nitrogen.

\* \* \* \* \*